United States Patent
Boxer et al.

(10) Patent No.: US 6,228,326 B1
(45) Date of Patent: May 8, 2001

(54) ARRAYS OF INDEPENDENTLY-ADDRESSABLE SUPPORTED FLUID BILAYER MEMBRANES

(75) Inventors: Steven G. Boxer, Stanford; Nick Ulman, Mountain View; Jay T. Groves, Stanford, all of CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 08/978,756

(22) Filed: Nov. 26, 1997

Related U.S. Application Data (60) Provisional application No. 60/032,325, filed on Nov. 29, 1996.

(51) Int. Cl.[7] ................................................. G01N 27/12
(52) U.S. Cl. ................................. 422/82.02; 422/82.06; 436/525
(58) Field of Search ........................ 422/68.1, 82.02, 422/82.06; 436/71, 525, 527, 528; 435/287.2, 287.1; 427/2.11, 2.13

(56) References Cited

U.S. PATENT DOCUMENTS

| | | | |
|---|---|---|---|
| 4,634,599 | * 1/1987 | Uzgiris | 427/2 |
| 5,192,507 | * 3/1993 | Taylor et al. | 422/68.1 |
| 5,204,239 | * 4/1993 | Gitler et al. | 435/7.1 |
| 5,234,566 | * 8/1993 | Osman et al. | 204/403 |
| 5,328,847 | * 7/1994 | Case et al. | 435/291 |
| 5,368,712 | 11/1994 | Tomich | 204/403 |
| 5,401,378 | 3/1995 | King | 204/418 |
| 5,494,803 | * 2/1996 | Carbonell et al. | 435/7.92 |
| 5,756,355 | * 5/1998 | Lang et al. | 435/7.21 |
| 5,846,814 | * 12/1998 | Galla et al. | 435/287.2 |

OTHER PUBLICATIONS

Bohorquez, Jaime H., et al., "Laser–Comparable Inkjet Text Printing", Hewlett–Packard Journal (9–17) Feb. 1994.

Evans, Evan et al., "Biomembrane Templates for Nanoscale Conduits and Networks", Science 273:933–935 (Aug. 16, 1996).

Groves, Jay T and Boxer Steven G., "Electric Field–Induced Concentration Gradients in Planar Supported Bilayers", Biophysical Journal 69:1972–1975 (Nov. 1995).

(List continued on next page.)

Primary Examiner—Jeffrey Snay
(74) Attorney, Agent, or Firm—Peter J. Dehlinger; Gregory L. Heinkel; Iota Pi Law Group (57) ABSTRACT

A surface detector array device suitable for use with a biosensor is disclosed. The device is formed of a substrate having a surface defining a plurality of distinct bilayer-compatible surface regions separated by one or more bilayer barrier regions. The bilayer-compatible surface regions carry on them, separated by a film of aqueous, supported fluid bilayers. The bilayers may contain selected receptors or biomolecules. A bulk aqueous phase covers the bilayers on the substrate surface.

18 Claims, 4 Drawing Sheets

OTHER PUBLICATIONS

Kühner, Martin et al., "Lipid Mono– and Bilayer Supported on Polymer Films: Composite Polymer–Lipid Films on Solid Substrates", Biophysical Journal, 67:217–226 (Jul. 1994).

Nowak, Rachel, "Entering the Postgenome Era", Science 270: 368–369 (Oct. 20, 1995).

Sackmann, E., "Supported Membranes: Scientific and practical Applications", Science 271:43–48 (Jan. 5, 1996).

Salamon, Zdzislaw and Tollin, Gordon, "Surface plasmon Resonance Studies of Complex Formation Between Cytochrome c and Bovine Cytochrome c Oxidase Incorporated into a Supported Planar Lipid Bilayer. 1. Binding of Cytochrome c to Cardiolipin/Phosphatidylcholine Membranes in the Absence of Oxidase", Biophysical Journal 71: 848–857 (Aug. 1996).

Stelzle, M., et al., "On the Application of Supported Bilayers as Receptive Layers for Biosensors with Electrical Detection", J. Phys. Chem. 97:2974–2981 (1993).

Stelzle, Martin and Sackmann, Erich, "Sensitive Detection of Protein Adsorption to Supported Lipid Bilayers by Frequency–dependent Capacitance Measurements and Microelectrophoresis", Biochimica et Biophysica Acta, 981:135–142 (1989).

Stelzle, M. et al., "Two–dimensional Microelectrophoresis in Supported Lipid Bilayers", Biophysical Journal 63:1346–1354 (Nov. 1992).

Stovel, Richard T. and Sweet, Richard G., "Individual Cell Sorting", The Journal of Histochemistry and Cytochemistry 27:284–488 (1979).

\* cited by examiner

ARRAYS OF INDEPENDENTLY-ADDRESSABLE SUPPORTED FLUID BILAYER MEMBRANES

This application claims benefit of provisional application Serial No. 60/032,325 filed Nov. 29, 1996.

This application was made with Government support under Contract No. N00014-91-J-1050 awarded by the Joint Services Electric Program of the Office of Naval Research, and Contract No. MCB-9506178 awarded by the National Science Foundation. Accordingly, the United States Government has certain rights in this invention.

FIELD OF THE INVENTION

The present invention relates in general to supported fluid bilayers and methods of confining them to selected areas. More specifically, the invention relates to microfabricated arrays of independently-addressable supported fluid bilayer membranes and their uses.

REFERENCES

Allen, T. M., et al., in STEALTH LIPOSOMES Chapter 20 (D. Lasic and F. Martin, Eds.) CRC Press, Boca Raton, Fla., (1995).

Arnold, F. H., Bio/Technol. 9:151–156 (1991).

Ausubel, F. M., et al., CURRENT PROTOCOLS IN MOLECULAR BIOLOGY, John Wiley and Sons, Inc., Media Pa. (1988).

Ballantyne, J. P., et al., J. Vac. Sci. Technol. 10:1094 (1973).

Barenholz, Y., et al., Biochemistry 16:2806–2810 (1977).

Blanchard, A., et al., Biosensors & Bioelectronics 11:687–690 (1996).

Brian, A. A., and McConnell, H. M., Proc. Natl. Acad. Sci. USA 81:6159 (1984).

Caras, et al., Science 238:1280–1283 (1987).

Case, et al., U.S. Pat. No. 5,192,507, issued Mar. 9, 1994.

Chan, P. Y., et al., J. Cell Biol. 115:245 (1991).

Cullen, D. C., et al., Biosensors 3:211–225 (1988).

Corsel, J. W., et al., J. Colloid. Interface Sci. 111:544–554 (1986).

Elender, et al., Biosensors and Bioelectronics 11:565–577 (1996).

Fodor, S. P. A., et al., Science 251:767 (1991).

Frey, W., et al., Proc. Natl. Acad. Sci. USA 93:4937 (1996).

Gitler, et al., U.S. Pat. No. 5,204,239, issued Apr. 20, 1993.

Groves, J. T., and Boxer, S. G., Biophys. J. 69:1972 (1995).

Groves, J. T., et al., Biophys. J. 71:2716 (1996).

Hamill, O. P., et al., Pflugers Arch. 391:85 (1981).

Haugland, R. P., in HANDBOOK OF FLUORESCENT PROBES AND RESEARCH CHEMICALS, 5th Ed., Molecular Probes, Inc., Eugene, Oreg. (1992).

Heath, T. D., Biochem. et Biophys. Acta 640:66 (1981).

Jönsson, U., et al., Colloids Surfaces 13:333–339 (1985).

Kern, W. and D. A. Puotinen, "Cleaning solution based on hydrogen peroxide for use in semiconductor technology" RCA Review (June) p. 187 (1970)

Khüner, et al., Biophys J. 67:217–226 (1994).

Krutenat, Kirk-Othmer 3rd Ed., Vol. 15, pp. 241–274 (1986).

Liedberg, B., et al., Z. Phys. 4:299–304 (1983).

Lin, A. Y., et al., Science 249:677–679 (1990).

Malik, S., et al., New J. Chem. 18:299–304 (1994).

Martin, F. J., Biochemistry 20:4229 (1981).

Martin, F. J., J. Biol Chem. 257:286 (1982).

Martin, F. J., in SPECIALIZED DRUG DELIVERY SYSTEMS—MANUFACTURING AND PRODUCTION TECHNOLOGY, (P. Tyle, Ed.) Marcel Dekker, N.Y., pp. 267–316 (1990).

McConnell, H. M., et al., Biochim. Biophys. Acta 864:95 (1986).

McHugh, et al., Proc. Natl. Acad. Sci. USA 92:8059–8063 (1995).

Nellen, Ph. M., and Lukosz, W., Sensors Actuators B1:592–596 (1990).

Osman, et al., U.S. Pat. No. 5,234,566, issued Aug. 10, 1993.

Petersen, K. E., Proceedings of the IEEE 70:420–457 (1982).

Sadler, D. M., et al., Biochemistry 23:2704–2712 (1984).

Sambrook, J., et al., MOLECULAR CLONING: A LABORATORY MANUAL, Cold Spring Harbor Laboratory Press, Vol. 2, Cold Spring Harbor Laboratory Press, Cold Spring Harbor, N.Y. (1989).

Schild, H., et al., Cell 76:29–37 (1994).

Shnek, D. R., et al., Langmuir 10:2382–2388 (1994).

Sigal, G. B., et al., Anal. Chem. 68:490 (1996).

Stelzle, M., and E. Sackmann, Biochim. Biophys. Acta 981:135 (1989).

Stelzle, M., et al., J. Phys. Chem. 97:2974–2981 (1993).

Szoka, F., Jr., et al., Ann. Rev. Biophys. Bioeng. 9:467 (1980).

Taylor, et al., U.S. Pat. No. 5,192,507, issued Mar. 9, 1993.

Tiberio, R. C., et al., Applied Physics Letters 62:476–478 (1993).

Thompson, L. F., et al., Eds., "Introduction to Microlithography", ACS Symposium Series, Washington D.C. (1983).

Tomich, et al., U.S. Pat. No. 5,368,712, issued Nov. 29, 1994.

Tözeren, A., et al., J. Cell Biol. 116:997 (1992).

Vroman, L., and Adams, A. L., Surface Sci. 16:438–446 (1969).

Watts, T. H., and McConnell, H. M., Ann. Rev. Immunol. 5:461 (1987).

Wettstein, et al., J. Exp. Med. 174:219–228 (1991).

Whitehorn, et al., Biotechnology 13:1215–1219 (1995).

Wolf, S., and Tauber, R. N., SILICON PROCESSING FOR THE VLSI ERA, Vol. 1, Lattice Press, Sunset Beach, Calif. (1986).

Xia, Y., et al., Science 273:347 (1996).

Zalipsky, S., et al., in POLY (ETHYLENE GLYCOL) CHEMISTRY: BIOTECHNICAL AND BIOMEDICAL APPLICATIONS (J. M. Harris, Ed.) Plenum Press, pg. 347–370 (1992a).

Zalipsky, S., et al., Biotechnol. Appl. Biochem. 15:100 (1992b).

Zalipsky, S., Bioconjugate Chemistry 4(4):296–299 (1993).

Zalipsky, S., et al., FEBS Letters 353:71–74 (1994).

Zalipsky, S., in STEALTH LIPOSOMES Chapter 9 (D. Lasic and F. Martin, Eds.) CRC Press, Boca Raton, Fla., (1995).

BACKGROUND OF THE INVENTION

Over the last several years, a number of highthroughput screening methods have been developed to facilitate the screening of thousands, if not millions, of compounds for a desired activity or activities. Such methods are typically based on detecting the binding of a potentially effective compound to a receptor. While these binding assays are effective at constraining the universe of compounds which may have the desired activity, they are typically not well-suited for evaluating this activity with any degree of detail.

The biological activity of potentially active compounds is typically evaluated using less efficient but more informative "secondary screens" or assays which typically require a substantial input of time by a trained technician or scientist. For evaluation of candidate compounds affecting integral membrane proteins such as receptors and ion channels, the amount of time required per compound may be several hours or days if the assay includes effects on electrophysiological activity. Accordingly, there is a need for a more efficient "secondary screen" of compounds affecting the activity of such integral membrane proteins, to identify those few compounds that justify further detailed analysis.

SUMMARY OF THE INVENTION

In one aspect, the present invention includes a surface detector array device. The device includes a substrate having a surface defining a plurality of distinct bilayer-compatible surface regions separated by one or more bilayer barrier regions, a bulk aqueous phase covering the substrate surface, a lipid bilayer expanse carried on each of the bilayer-compatible surface regions, and an aqueous film interposed between each bilayer-compatible surface region and corresponding lipid bilayer expanse. In a general preferred embodiment, the bilayer-compatible surface regions and the bilayer barrier surface regions are formed of different materials.

The bilayer-compatible surface region may be formed from any of a variety of materials having such bilayer-compatible surface properties, including $SiO_2$, $MgF_2$, $CaF_2$, and mica, as well as a polymer film, such as a polyacrylamide or dextran film. $SiO_2$ is a particularly effective material for the formation of a bilayer-compatible surface region.

The bilayer barrier surface region may be formed from any of a variety of materials having such bilayer barrier surface properties, including gold, positive photoresist and aluminum oxide.

In a general embodiment, the lipid bilayer expanse contains at least one lipid selected from the group consisting of phosphatidylcholine, phosphatidylethanolamine, phosphatidylserine, phosphatidic acid, phosphatidylinositol, phosphatidylglycerol, and sphingomyelin.

In one embodiment, the device contains between about 10 and about 100 distinct bilayer-compatible surface regions. In another embodiment, the device contains at least about 2500 distinct bilayer-compatible surface regions. In yet another embodiment, the device contains at least about 25,000 distinct bilayer-compatible surface regions. In still another embodiment, the device contains at least about 2.5 million distinct bilayer-compatible surface regions.

The bilayer-compatible surface regions are separated from one another, in one general embodiment, by bilayer barrier regions that are between about 1 $\mu$m and about 10 $\mu$m in width.

The lipid bilayer expanses on different bilayer-compatible surface regions may have different compositions, and may further include a selected biomolecule, with different expanses having a different biomolecule, such as transmembrane receptor or ion channel. The biomolecule may be covalently or noncovalently attached to a lipid molecule. Examples of non-covalent interactions include electrostatic and specific molecular interactions, such as biotin/streptavidin interactions. Examples of biomolecules include proteins, such as ligands and receptors, as well as polynucleotides and other organic compounds.

In another aspect, the invention includes a method of forming a surface detector device having a plurality of independently-addressable lipid bilayer regions. The method includes the steps of (i) treating a planar substrate to form a substrate surface defining a plurality of distinct bilayer-compatible surface regions separated by one or more bilayer barrier regions, and (ii) applying a suspension of lipid bilayer vesicles to the plurality of distinct bilayer-compatible surface regions under conditions favorable to the formation of supported bilayers on the bilayer-compatible surface regions. The applying then results in the formation of supported bilayer membranes on the bilayer-compatible surface regions.

In yet another aspect, the invention includes a method for detecting a selected ligand in a mixture of ligands. The method includes the steps of (i) contacting the mixture with a biosensor surface detector array device such as described above, and (ii) detecting binding of the selected ligand to receptors which specifically bind it.

In still another aspect, the invention includes a surface detection array device for use in a biosensor. Such a device includes (i) a substrate having a surface defining a plurality of distinct bilayer-compatible surface regions separated by one or more bilayer barrier regions, (ii) a bulk aqueous phase covering the substrate surface, (iii) a lipid bilayer expanse carried on each of the bilayer-compatible surface regions, and (iv) an aqueous film interposed between each bilayer-compatible surface region and corresponding lipid bilayer expanse. Each bilayer expanse contains a specie of receptor or biomolecule, and different bilayer expanses contain different species of receptors or biomolecules.

These and other objects and features of the invention will become more fully apparent when the following detailed description is read in conjunction with the accompanying drawings.

DETAILED DESCRIPTION OF THE INVENTION

I. Definitions

The terms below have the following meanings unless indicated otherwise.

The term "aqueous" refers to a water-based liquid medium that is not deleterious to lipids.

A "receptor" is a macromolecule capable of specifically interacting with a ligand molecule. In cells, receptors are typically associated with lipid bilayer membranes, such as the extracellular, golgi or nuclear membranes. Receptors for incorporation into expanses of lipids in vitro (e.g., supported bilayers) may either be purified from cells, recombinantly expressed, or, in the case of small receptors, chemically synthesized.

A "ligand" is a molecule capable of specifically binding to a receptor. Binding of the ligand to the receptor is typically characterized by a high binding affinity, i.e., $K_m > 10^5$, and can be detected either as a change in the receptor's function (e.g., the opening of an ion channel associated with or part of the receptor) or as a change in the immediate environment of the receptor (e.g., detection of binding by surface plasmon resonance). Ligands for incorporation into expanses of lipids in vitro (e.g., supported bilayers) may either be purified from cells, recombinantly expressed, or, in the case of small ligands, chemically synthesized.

Binding is "specific" if it results from a molecular interaction between a binding site on a receptor and a ligand, rather than from "non-specific" sticking of one protein to another. In cases where the ligand binds the receptor in a reversible manner, specificity of binding can be confirmed by competing off labeled ligand with an excess of unlabeled ligand according to known methods. Non-specific interactions can be minimized by including an excess of a protein (e.g., BSA) that does not have binding sites for either the ligand or receptor.

II. Surface Detector Array Device

Figure 1:
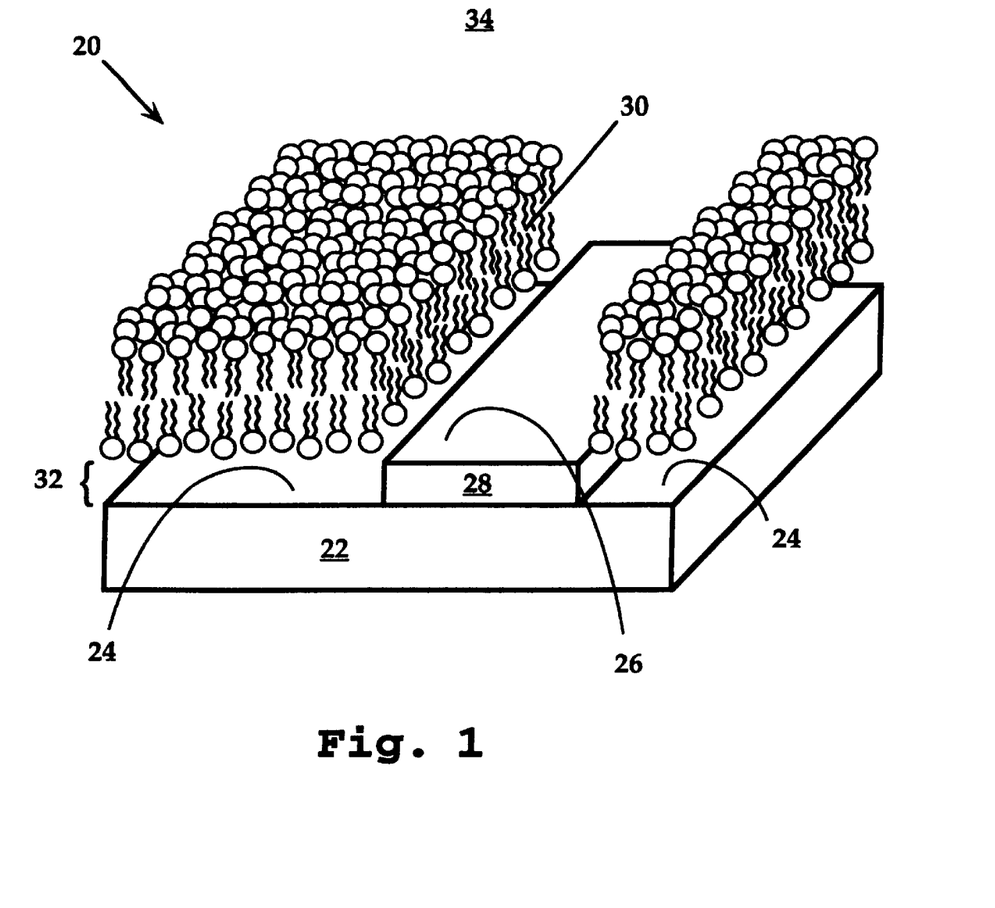
FIG. 1 shows a portion of a surface detector array device (SDAD) of the invention.

FIG. 1 is a perspective view of a portion of a surface detector array device (SDAD) 20 in accordance with the invention. The device is fabricated from a substrate 22, such as an oxidized silicon or fused silica wafer. The dimensions of the substrate are typically between about 0.5 cm to about 5 cm per side and about 0.1 mm to about 1 cm in thickness.

The substrate surface contains a plurality of distinct bilayer-compatible surface regions 24 separated by one or more bilayer barrier regions 26. The bilayer barrier region(s) 26 are preferably formed of a material 28 different from the material 22 forming the bilayer-compatible surface regions 24.

A lipid bilayer expanse 30 is carried on each of the bilayer-compatible surface regions 24. Interposed between each bilayer-compatible surface region 24 and corresponding lipid bilayer expanse 30 is an aqueous film 32 that is between about 5 Å and 15 Å (typically about 10 Å) in thickness. Covering the substrate surface and lipid expanses is a bulk aqueous phase 34.

The bilayer barrier regions may be depressed, flush, or elevated (as shown at 26 in FIG. 1), with respect to the bilayer-compatible surface 24. In embodiments having elevated barriers, the height of the barrier may range from tens of Angstroms to several micrometers or more. The width of the barriers is typically between about 100 nm and about 250 μm. Preferably, the width is between about 1 and 100 μm.

According to results of experiments performed in support of the invention, the lipid barrier regions do not function simply by mechanical or physical separation of adjacent lipid bilayer regions. Rather, the experiments indicate that the characteristics which allow a surface to act as a bilayer barrier region are chemical/electrostatic properties intrinsic to the material making up the surface. Examples of such chemical/electrostatic properties include hydrophobicity, dielectric permeability, conductivity, and surface charge density.

Similarly, the degree of "bilayer-compatibility" of a selected surface is a function of its intrinsic material properties rather than its shape. The interactions between membranes and surfaces involve electrostatic and hydration forces as well as attractive contributions from long-range van der Waals forces. In a suitable bilayer-compatible surface, an energetic minimum traps the bilayer membrane between about 5 Å and 15 Å (typically about 10 Å) away from the supporting surface, separated from the supporting surface by an aqueous film of corresponding thickness. Bilayer-compatible surfaces are typically hydrophilic.

Functionally, the suitability of a material for use as a bilayer barrier surface region or a bilayer-compatible surface region may be evaluated by the material's performance in a simple "fluorescence recovery after photobleaching" (FRAP) test as follows:

A small sample of the material (e.g., a portion having a ~1 $cm^2$ flat surface) is cleaned or treated as described herein (e.g., using exposure to argon plasma or, for materials which can tolerate it, an acids wash). The surface is then rinsed and a selected amount (e.g., 50 μl) of a suspension of lipid vesicles containing a fluorescent marker (prepared as described in the Materials and Methods) is applied to the surface. The suspension is allowed to remain in contact with the surface for several minutes (e.g., 5 min). The surface is then immersed in an aqueous medium to rinse off or substantially dilute the suspension (e.g., by adding ~100 ml of distilled water or PBS), and the surface is transferred to the stage of a standard fluorescence microscope. A portion of the surface is then exposed to a bright light (e.g, from a 100W mercury arc lamp) sufficient to bleach the fluorescent moieties of the reporter exposed to the light (e.g., about 1 min., depending on the fluorophore), and the surface is monitored under the microscope for ~10 minutes (depending on size of the bleached spot) to assess recovery of fluorescence.

When the above test is carried out using a material capable of forming a bilayer-compatible surface, vesicles in the suspension will have fused with the surface forming a supported bilayer containing the fluorescent reporter, and the localized exposure to photobleaching light will have bleached the area of the bilayer corresponding to the region of the surface on which the photobleaching light was focused. During the monitoring period, fluorescence in the bleached area of the bilayer will recover due to the fluidity of the supported bilayer.

In contrast, when the above test is carried out using a material that forms a bilayer-barrier surface, vesicles in the suspension will not have fused with the surface to form a fluid bilayer. Under such conditions, the vesicles will either be rinsed off during the rinse step or will remain attached and immobilized on the surface. If the vesicles rinse off, little or no fluorescence will be observed. If the vesicles stick to the surface but do not form a fluid bilayer, fluorescence will not be recovered in the bleached area following photobleaching. In either case, the material is an effective bilayer barrier material. It will be appreciated, however, that the use of materials to which the vesicles do not stick is preferable to the use of those which, following the above FRAP test, contain immobilized lipid or membrane material.

The above test can be carried in parallel with a number of different materials that the practitioner of the invention may have at hand. In this way, in a matter of a few hours, the practitioner can readily determine whether a particular material will be effective to form a surface that is either bilayer-compatible or serves as a bilayer barrier.

It will be appreciated that essentially all materials suitable for use in the microfabrication of a device according to the invention will, when cleaned, present either a bilayer-compatible surface region or a bilayer-barrier surface region. Accordingly, application of the simple FRAP test described above will typically yield a material useful in the practice of the invention with each material tested.

Exemplary materials having properties making them suitable for lipid bilayer barriers include certain polymers (e.g., photoresist) and various metals (e.g., gold) and minerals (e.g., aluminum oxide). An advantage of photoresist is that it is relatively easy to pattern with a photomask and is non-conductive. Aluminum oxide has the advantage of being both nonconductive and reusable, withstanding most cleaning procedures.

Exemplary materials having properties making them suitable for bilayer-compatible surfaces include various glasses, silicon oxides, including oxidized silicon ($SiO_2$), $MgF_2$, $CaF_2$, mica, and various polymer films, such as thin polyacrylamide or dextran films (see, e.g., Elender, et al., 1996; Khuner, et al., 1994), both incorporated herein by reference). Both types of polymer films form a suitable bilayer-compatible surface that is hydrated to provide a film of aqueous between the polymer film and the supported bilayer membrane.

To generate a substrate surface that is "bilayer-compatible", the surface is typically cleaned and/or treated to remove surface impurities (dirt, oils, etc.). Suitable treatments are discussed below with respect to the making or construction of a device of the invention.

The supported bilayer itself is a self-assembling, two-dimensional fluid system, typically consisting of two opposed leaflets of vesicle-forming lipid molecules. However, it can be constructed as described below from any suitable membrane-forming amphiphile, including proteins and nonlipids.

Most vesicle-forming lipids are long-chain carboxylic acids, such as glycerides, having the hydroxyl groups of the glycerol esterified with (i) fatty acid chain(s), and (ii) a charged or polar moiety, such as a phosphate-ester group. The vesicle-forming lipids are preferably ones having two hydrocarbon chains, typically acyl chains, and a polar head group. Long-chain carboxylic acids with a phosphate group, or phospholipids, are particularly well-suited for use with the present invention.

There are a variety of synthetic vesicle-forming lipids and naturally-occurring vesicle-forming lipids, including the phospholipids, such as phosphatidylcholine (PC), phosphatidylethanolamine (PE), phosphatidylserine (PS), phosphatidic acid, phosphatidylinositol (PI), phosphatidylglycerol (PG), and sphingomyelin, where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Preferred diacyl-chain lipids for use in the present invention include diacyl glycerol, phosphatidyl ethanolamine (PE) and phosphatidylglycerol (PG). These lipids are preferred for use as the vesicle-forming lipid, the major liposome component, and for use in the derivatized lipid described below. All of these phospholipids and others are available from specialized suppliers of phospholipids (e.g., Avanti Polar Lipids, Inc., Alabaster, Ala.) as well as from general chemical suppliers, such as Sigma Chemical Co. (St. Louis, Mo.).

The aqueous film and bulk aqueous phase may be any suitable aqueous solution, such as a buffered saline solution (e.g., PBS). The bulk solution can be readily changed (taking care, of course, to keep the supported bilayer submerged at all times) by, e.g., flow-through rinsing with a solution having a different composition.

Figure 4:
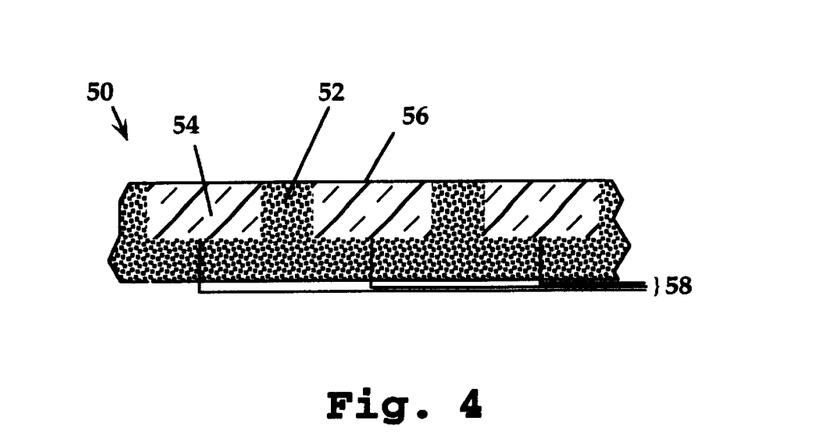
FIG. 4 shows the structural portion of a device of the invention suitable for use in a biosensor.

As described above, FIG. 1 shows a support grid microfabricated from a wafer of a material which forms the bilayer-compatible surfaces of the device. A device may also be microfabricated, however, from a wafer of a material which forms the bilayer-barrier surface regions of the device. One embodiment of such a device is shown in FIG. 4. Here, the structural portion 50 of a device of the invention is produced by microfabricating a wafer of a bilayer barrier material 52 (e.g., aluminum oxide) to contain regions, such as region 54, consisting of a bilayer-compatible material, where each region corresponds to one of the plurality of distinct bilayer-compatible surface regions, such as region 56. In one embodiment, the regions 54 are electrically-conductive and are connected to leads 58 which can be used to record changes in the membrane potential at the surface. An example of an electrically-conductive bilayer-compatible material is a metal, such as gold, coated with a thin film of silicon oxide or polymer material to make the surface bilayer-compatible. The thin film of silicon oxide, while not an electrical conductor, can effectively pass capacitative current.

Alternatively or in addition, electrodes having a bilayer-compatible surface may be generated from standard doped (e.g., boron-doped) silicon wafers. A layer of silicon oxide may be formed on such wafer substrates to provide a bilayer-compatible surface, under which resides a semiconductor (doped silicon) electrode. The semi-conductor electrode can, of course, be interfaced with any of a variety of other elements, e.g., semi-conductor elements in the substrate itself or in a separate chip, as desired, to facilitate or enhance the processing of information from the patch of bilayer membrane corresponding to that electrode.

A number of different devices have been produced in accordance with the invention. They include the following (i) a device containing a 1 $cm^2$ array of 2500 identical 200 $\mu$m square corrals or regions, (ii) a device containing a 1 $cm^2$ array of 10,000 identical 100 $\mu$m square regions, (iii) a device containing a 1 $cm^2$ array of about 37,000 identical 50 $\mu$m square regions separated by 2 $\mu$m barriers of photoresist, and (iv) a device containing a 1 $cm^2$ array of about 2.8 million 5 $\mu$m square corrals or regions separated by 1 $\mu$m-wide barriers of photoresist.

Exemplary embodiments of the invention include devices where the bilayer lipid expanses contain different biomolecules, such as receptor protein molecules, ligand protein molecules, or other protein molecules. Such devices are particularly useful in biosensors, described more fully in the applications section of the specification, and are made as described below by fusing proteoliposomes to the bilayer-compatible surface.

It is recognized that proteoliposome vesicles can be fused to a glass surface to create a planar supported membrane (Brian and McConnell, 1984). This technique has been successfully applied in a number of situations. In one example, the H-2K$^k$ protein was reconstituted into egg phosphatidylcholine-cholesterol vesicles by detergent dialysis, and the vesicles were used to create a planar membrane on glass (Brian and McConnell, 1984). The H-2K$^k$-containing membrane was capable of eliciting a specific cytotoxic response when brought into contact with a cell.

Chan, et al. (1991) demonstrated that a glycosylphosphatidylinositol (GPI)-anchored membrane receptor is laterally mobile in planar membranes formed from proteoliposome fusion, and that this mobility enhances cell adhesion to the membrane. Other applications employ a combination of vesicle fusion, Langmuir-Blodgett methodology and derivatized surfaces to prepare supported membranes (Sui, et al., 1988; Plant, et al., 1995).

In addition to incorporation of receptors or ion channels into the bilayer membrane, the bilayer may be derivatized with any of a number of groups or compounds to create a surface having the desired properties. For example, the liposomes may contain a ligand bound to the surface of the lipid by attachment to surface lipid components. Generally, such a ligand is coupled to the polar head group of a vesicle-forming lipid. Exemplary methods of achieving such coupling are described below.

III. Construction of a Surface Detector Device with Independently-Addressable Lipid Bilayer Regions Surface detector device of the invention may be conveniently produced using a combination of microfabrication and lipid vesicle technologies, e.g., as described in Example 1.

A. Microfabrication of Patterned Support Grid

Patterning of the substrate to produce a substrate surface having a plurality of distinct bilayer-compatible surface regions separated by one or more bilayer barrier regions may be done in a number of different ways appreciated by those knowledgeable in the microfabrication arts having the benefit of the resent specification. For instance, micromachining methods well known in the art include film deposition processes, such as sputtering, spin coating and chemical vapor deposition, laser fabrication or photolithographic techniques, or etching methods, which may be performed by either wet chemical or plasma processes. These and other micromachining methods are summarized, for example, in Petersen (1982), incorporated herein by reference. General silicon processing techniques known in the art are described, for example, in Wolf and Tauber (1986) incorporated herein by reference.

A device is typically produced by first selecting a substrate material and producing a patterned support grid (the structural portion of a surface detector array device of the invention). The support grid carries on the patterned side the substrate surface according to the invention. The substrate is typically of a material selected to have the properties of one of either a bilayer-compatible or bilayer barrier material with strips of a material having the properties of the other of a bilayer-compatible or bilayer barrier material. In one general embodiment, a bilayer-compatible substrate material is patterned with strips of a bilayer-barrier material. In another general embodiment, the substrate material is a bilayer barrier material and its surface is patterned with regions of a bilayer-compatible material. It will be appreciated, however, that the substrate material can be patterned with both regions of bilayer-compatible material and regions of bilayer barrier material, such that the original substrate material is not represented at the patterned substrate surface. The materials which do form the substrate surface are selected such that after surface cleaning and/or treating, one yields a bilayer-compatible surface region and the other yields a bilayer barrier surface region.

Photoresist has at least two potential uses with respect to the present invention. As discussed above, positive photoresist is an effective bilayer-barrier material. Of course, photoresist can also be used in the traditional sense of patterning a substrate for subsequent lithography to generate microfabricated devices of the invention. Suitable negative- or positive-resist materials are well known. Common negative-resist materials include two-component bisarylazide/rubber resists, and positive-resist materials include two-component diazoquinone/phenolic resin materials. An example of electron beam resist, which may also be suitable, includes polymethylmethacrylate (PMMA) see, e.g., Thompson, et al. (1983).

As mentioned above, silicon is a preferred substrate material because of the well-developed technology permitting its precise and efficient fabrication, but other materials may be used, including polymers such as polytetrafluoroethylenes. The substrate wafer (e.g., silicon wafer) is typically cleaned using a standard RCA clean (Kern and Puotinen, 1970; Wolf and Tauber, 1986). The wafer is then oxidized at a temperature of between about 800 and 1000° C. in steam using known methods (Wolf and Tauber, 1986) until a layer of oxide (preferably about 0.5 μm in thickness) is formed. The oxide layer is then coated with a photoresist layer preferably about 1 μm in thickness. As described herein, this method can be used to produce the structural portion of an exemplary surface detector array device of the invention, which now only needs to be cleaned as described below before it is exposed to a vesicle suspension to generate the bilayer expanses.

Alternatively, the photoresist-patterned substrate can be subjected to standard photolithography to produce a surface detector array device with a material other than photoresist forming the bilayer-barrier regions. In this case, the coated laminate is irradiated through a photomask imprinted with a pattern corresponding in size and layout to the desired pattern. Methods for forming photomasks having desired photomask patterns are well known. For example, quartz plates can be patterned with chrome with electron beam machine and an electron beam resist, such as PBS, using standard methods. Alternatively, a mask can be obtained commercially from any of a number of suppliers, e.g., Align-Rite (Burbank, Calif.). Exposure is carried out on a standard contact mask aligner machine, such as a Karl Suss contact lithography machine. Conventional positive or negative photoresists may be used with clear-field or dark-field photomasks. The pattern may be transferred to the substrate by subsequent etching or liftoff processes.

Electrodes may be fabricated into the device using any of a number of different techniques are available for applying thin metal coatings to a substrate in a desired pattern. These are reviewed in, for example, Krutenat, 1986; and in Wolf and Tauber, 1986, both incorporated herein by reference. Convenient and common techniques used in fabrication of microelectrodes include vacuum deposition, evaporation, sputtering, and plating. Various conductive materials, including doped silicon and metals such as platinum, gold, or silver may be used for the electrodes.

Deposition techniques allowing precise control of the area of deposition are preferred for application of electrodes to the selected regions of the device. Such techniques are described, for example, in Krutenat, above, and in Wolf and Tauber. They include physical vapor deposition using an electron beam, where atoms are delivered on line-of-sight to the substrate from a virtual point source. In laser coating, a laser is focused onto the target point on the substrate, and a carrier gas projects powdered coating material into the beam, so that the molten particles are accelerated toward the substrate.

Another technique allowing precise targeting uses an electron beam to induce selective decomposition of a previously deposited substance, such as a conventional electron beam resist (e.g., PMMA), a thin layer of another material (e.g., a metal salt), a monolayer, or the like (see, e.g., Tiberio, et al., 1993). This technique has been used to produce sub-micron circuit paths (e.g., Ballantyne, et al., 1973). It will be appreciated that the dimensions of the different regions can be made extremely small, since electron beam lithography along with near field scanning microscopy may be used to generate and image membrane patterns on the nanometer scale. Further, certain nontraditional microfabrication materials having bilayerbarrier properties can be patterned using standard technologies. For example, aluminum oxide can be patterned on $SiO_2$ substrate wafers by evaporation and liftoff (Wolf and Tauber, 1986, see p. 535). Such patterning, as well as the general microfabrication described above, can be conveniently done by contracting the work out to a company offering microfabrication services, such as MCNC (Research Triangle Park, N.C.), IC Sensors (Milpitas, Calif.) and Silica-Source Technology (Tempe, Ariz.).

B. Cleaning of Patterned Support Grid

After the patterned support grid is made, it is cleaned and/or treated to strip or etch off any impurities or contaminants present on the substrate surface which might otherwise inhibit the formation of a lipid bilayer adjacent the surface. The cleaning procedure is selected such that it does not substantially damage the functionality of the bilayer barrier regions. For example, embodiments where the barrier regions are made of photoresist should not be cleaned using the traditional pirhana solution acid wash (3:1 $H_2SO_4:H_2O_2$), since the acid can strip off the bilayer barrier regions. An exemplary cleaning/treating process that does not damage photoresist employs exposure of the patterned grid to argon or oxygen plasma for several minutes. Although the plasma does etch the photoresist somewhat, it strips off contaminants from the surface layer of the substrate (e.g., $SiO_2$ substrate) before substantially damaging the photoresist layer.

A number of suitable etching and/or cleaning procedures are known in the art. Four such procedures are summarized below. They include those described above and may be employed separately or in combination. In the first method, the structural portion of the device (support grid) is baked at 500° C. for several hours. This method is not compatible with gold or photoresist. In the second method, the support grid is washed in pirhana solution acid wash (3:1 $H_2SO_4:H_2O_2$). This method is not compatible with photoresist and many metals, although it can be successfully used with gold and platinum. In the third method, the support grid is boiled in detergent (e.g., 7X detergent from ICN Biomedicals, Inc. (Aurora, Ohio), diluted 1:4). This method is not compatible with photoresist and is not very effective used alone. In the fourth method, the support grid is etched in a gas plasma (e.g., argon or oxygen). This method works most effectively when combined with the third method, but can be used alone; it is the only procedure described herein that is suitable for use with photoresist.

C. Making Supported Bilayer Expanses

Following such a wash/etching/treatment step, the grid is placed in a chamber and a suspension of vesicles or liposomes formed of a selected lipid and (optionally) containing selected proteins or other biomolecules is contacted with each bilayer-compatible surface region. Vesicles in the suspension generally fuse with the bilayer-compatible surface region within minute or less to form a supported bilayer membrane (Xia, et al., 1996; Groves, et al., 1996). A humidified chamber is preferably used in applications where the volume of the drops of lipid suspension is small enough (e.g., ~<5 $\mu l$) to allow substantial evaporation before the bilayers form and the grid is flooded with bulk aqueous.

Liposomes may be prepared by a variety of techniques, such as those detailed in Szoka, Jr., et al. (1980). The lipid components used in forming liposomes useful in making the present invention preferably contain at least 70 percent vesicle-forming lipids. In one general embodiment, the bilayers are formed as described in Example 1.

As discussed above, the supported bilayers may contain receptors of other biomolecules, such as peptides, nucleic acids, factors, etc., attached to or incorporated into the supported bilayer membrane. Methods for producing such "modified" bilayers using "derivatized" liposomes, or liposomes containing an additional moiety such as a protein, are well known (see, e.g., Zalipsky, 1995; Allen, et al., 1995, as well as U.S. Pat. Nos. 6,605,630, 4,731,324, 4,429,008, 4,622,294 and 4,483,929). A few examples are discussed below.

One procedure suitable for preparation of such derivatatized liposomes involves diffusion of polymerlipid conjugates into preformed liposomes. In this method, liposomes are prepared from vesicle-forming lipids as described, and the preformed liposomes are added to a solution containing a concentrated dispersion of micelles of polymer-lipid conjugates. The mixture is then incubated under conditions effective to achieve insertion of the micellar lipids into the preformed liposomes.

In another method, the biomolecule is coupled to the lipid, by a coupling reaction described below, to form an biomolecule-lipid conjugate. This conjugate is added to a solution of lipids for formation of liposomes, as will be described. In another method, a vesicle-forming lipid activated for covalent attachment of a biomolecule is incorporated into liposomes. The formed liposomes are exposed to the biomolecule to achieve attachment of the biomolecule to the activated lipids. In yet another method, particularly suitable for making liposomes containing integral membrane receptors or proteins, the liposomes are simply formed in the presence of such proteins to make "proteoliposomes, as described below.

A variety of methods are available for preparing a conjugate composed of a biomolecule and a vesicle-forming lipid. For example, water-soluble, amine-containing biomolecules can be covalently attached to lipids, such as phosphatidylethanolamine, by reacting the amine-containing biomolecule with a lipid which has been derivatized to contain an activated ester of N-hydroxysuccinimide.

As another example, biomolecules, and in particular large biomolecules such as proteins, can be coupled to lipids according to reported methods. One method involves Schiff-base formation between an aldehyde group on a lipid, typically a phospholipid, and a primary amino acid on the biomolecule. The aldehyde group is preferably formed by periodate oxidation of the lipid. The coupling reaction, after removal of the oxidant, is carried out in the presence of a reducing agent, such as dithioreitol, as described by Heath (1981). Typical aldehyde-lipid precursors suitable in the method include lactosylceramide, trihexosylceramine, galacto cerebro-side, phosphatidylglycerol, phosphatidylinositol and gangliosides.

A second general coupling method is applicable to thiol-containing biomolecules, and involves formation of a disulfide or thioether bond between a lipid and the biomolecule. In the disulfide reaction, a lipid mine, such as phosphatidylethanolamine, is modified o contain a pyridylditho derivative which can react ith an exposed thiol group in the biomolecule. Reaction conditions for such a method can be found in Martin (1981). The thioether coupling method, described by Martin (1982), is carried out by forming a sulfhydryl-reactive phospholipid, such as N-(4)P-maleimido-phenyl(butyryl)phosphatidylethanolamine, and reacting the lipid with the thiol-containing biomolecule.

Another method for reacting a biomolecule with a lipid involves reacting the biomolecule with a lipid which has been derivatized to contain an activated ester of N-hydroxysuccinimide. The reaction is typically carried out in the presence of a mild detergent, such as deoxycholate. Like the reactions described above, this coupling reaction is preferably performed prior to incorporating the lipid into the liposome.

Methods for attachment of a biomolecule to the liposome through a short spacer arm have been described, such as in U.S. Pat. No. 4,762,915. In general, attachment of a moiety to a spacer arm can be accomplished by derivatizing the vesicle-forming lipid, typically distearol phosphatidylethanolamine (DSPE), with a hydrophilic polymer, such as polyethylene glycol (PEG), having a reactive terminal group for attachment of an affinity moiety. Methods for attachment of ligands to activated PEG chains are described in the art (Allen, et al., 1995; Zalipsky, 1992a; Zalipsky, 1992b; Zalipsky, 1993; Zalipsky, 1994). In these methods, the inert terminal methoxy group of mPEG is replaced with a reactive functionality suitable for conjugation reactions, such as an amino or hydrazide group. The end functionalized PEG is attached to a lipid, typically DSPE. The functionalized PEG-DSPE derivatives are employed in liposome formation and the desired ligand (i.e., biomolecule) is attached to the reactive end of the PEG chain before or after liposome formation.

Another method of linking biomolecules such as proteins to a supported lipid bilayer is via specific interactions between the side chain of the amino acid histidine and divalent transition metal ions (Malik, et al., 1994; Arnold, 1991) immobilized on the membrane surface. This method has been used, for example, to attach various proteins and peptides to lipid monolayers (Shnek, et al., 1994; Frey, et al., 1996; Sigal, et al., 1996). Briefly, a cDNA encoding the ligand or receptor which is to immobilized to the bilayer surface is engineered so that the ligand or receptor contains a poly-histidine (e.g., hexa-histidine) tag at one of its termini (e.g., the C-terminus). The bilayer is formed of or derivatized with metal-chelating moieties (e.g., copper-chelating moieties or lipids (Shnek, et al., 1994; Frey, et al., 1996)), and the expressed His-tagged protein is incubated with the vesicles used to generate the supported bilayer, or with the supported bilayer itself.

Specific high-affinity molecular interactions may also be employed to link selected biomolecules to a 30 supported bilayer. For example, a bilayer expanse may be formed to include biotinylated lipids (available from, e.g., Molecular Probes, Eugene, Oreg.), and a biomolecule linked or coupled to avidin or steptavidin may be linked to the bilayer via the biotin moieties.

Biomolecules may also be linked to a supported lipid bilayer via glycan-phosphatidyl inositol (GPI). The proteins to be linked can be genetically engineered to contain a GPI linkage (Caras, et al., 1987; Whitehorn, et al., 1995). Incorporation of a GPI attachment signal into a gene will cause the protein to be post-translationally modified by the cell resulting in a GPI linkage at the signal position. It will be appreciated that this type of alteration generally does not affect the molecular recognition properties of proteins such as the ones described here (Lin, et al., 1990; McHugh, et al., 1995; Wettstein, et al., 1991).

A convenient approach is to clone the cDNA sequence encoding the protein of interest into a vector containing the GPI attachment signal using standard molecular biology methods and procedures (see, e.g., Ausubel, et al., 1988; Sambrook, et al., 1989). An exemplary vector is the pBJ1Neo derivative described in Whitehorn, et al., (1995), which contains a modified polylinker and the human placental alkaline phosphatase (HPAP) GPI linkage signal. Another suitable vector is pBJ1Neo (Lin, et al., 1990). The construct is then transfected into suitable host cells (e.g., Chinese hamster ovary (CHO) cells) using a standard transfection method, such as electroporation (e.g., using settings of ~0.23 kV/960 $\mu$F). Transfected cells are selected, e.g., using fluorescence activated cell sorting (FACS) with an antibody directed against the protein of interest.

Transfected CHO cells with high surface expression are expanded in culture. GPI-linked proteins are purified from the cell membrane fraction by, e.g., detergent extraction (Schild, et al., 1994). Briefly, almost confluent CHO cells are washed free of medium with PBS containing a cocktail of proteinase and phosphatase inhibitors. The cells are lysed on ice in the same buffer containing 0.5% NP40. Nuclei and cell debris are spun out and the supernatant is loaded on an antibody affinity column.

The detergent is then exchanged to 1% Octoglucoside (OG) on the column, and the proteins are eluted by base (pH 11.5) containing 1% OG. After elution, the proteins are either stored in neutralized elution buffer or the buffer is exchanged with 1% OG in PBS. The purified GPI-linked proteins, or any other desired proteins or receptors, may then be incorporated into proteoliposomes as described below.

Proteoliposomes containing a selected membrane protein may be prepared using standard methods, e.g., using the protocol described by Sadler, et al. (1984). In this method, recombinant receptor proteins are concentrated in a suitable buffer (e.g., 10 mM Tris pH 8.0, 0.1% LDAO buffer) using, for example, a DEAE ion-exchange column or Centricon concentrator (Amicon Co., Beverly, Mass.). If desired, the salt concentration may be adjusted to a desired value (e.g., 100 mM NaCl) by dialysis.

The concentrated receptor proteins are then added to a suspension of small unilamellar vesicles (SUVs; prepared as described below; optionally with a lipid label such as Texas Red), e.g., in a small conical-bottom vial with stirring, to a selected final RC:lipid mole ratio. The ratio is generally between about 1:100 and 1:1000, preferably between about 1:300 and 1:500, In one embodiment, the ratio is 1:350.

In the case of the GPI-linked proteins described above, the proteins, at concentrations of around 100 nM, are mixed with SUVs, at a lipid concentration of 1 mM, in TN25/50, with the total OG concentration preferably not exceeding 0.15%. The detergent may removed by dialysis against three changes of 1 liter TN25/50 at 4° C. After dialysis, the lipid concentration may be determined using the NBD-PE absorption at 465 nm and adjusted to 0.2 mg/ml.

Alternatively, the samples may be run on a Sepharose column (e.g., a Sepharose CL-4B (Sigma) column), previously equilibrated with SUVs to minimize lipid adsorption, and fractions are collected. The absorption spectra of the proteoliposome fractions are measured, and the true protein:lipid mole ratio calculated using the absorption peak of the lipid label.

Typically, the mole ratio of protein:lipid in the fractions follows a monotonic decrease, beginning at about 1:300 and ending at about 1:1000–1200. Only the fractions with a mole ratio of about 1:500 or lower are generally used to make planar supported bilayers; the fractions with higher mole ratios do not always form uniform planar bilayers.

IV. Applications

A. Biosensors

In one aspect, the invention includes a biosensor having a surface detection array device. The detection array device comprises (i) a substrate having a surface defining a plurality of distinct bilayer-compatible surface regions separated by one or more bilayer barrier regions, (ii) a bulk aqueous phase covering the substrate surface, (iii) a lipid bilayer expanse carried on each of the bilayer-compatible surface regions, and (iv) an aqueous film interposed between each bilayer-compatible surface region and corresponding lipid bilayer expanse, where each bilayer expanse contains a specie of receptor or biomolecule, and different bilayer expanses contain different species of receptors or biomolecules. The receptor or biomolecule is anchored to or in each lipid bilayer expanse. The specific binding of a particular ligand to a receptor in a lipid expanse is detected by any of a variety of known biosensor detection mechanisms, such as optical or electrical detection.

In biosensors employing electrical detection, the support grid preferably contains a conductive electrode and electronic lead for each array element of the device. The leads typically terminate as extensions or "pins" from the device, which can be interfaced with a connector cable or ribbon leading to a processor. The electrodes preferably form at least a portion of the bilayer-compatible surface and are separated from one another by strips of insulating material. They can be used to detect capacitative as well as conductive current transients. In one embodiment, the electrodes form a portion of the bilayer-compatible surface. In another embodiment, the construction of which is detailed in Example 5, the electrodes are positioned just beneath the bilayer-compatible surface, i.e., the electrode surface is coated with a thin layer of material, such as low-temperature grown oxide (e.g., $SiO_2$), which forms the bilayer-compatible surface. In embodiments where this layer is an insulating material, it is preferably less than about 1 $\mu$m in thickness to enable the detection of capacitative transients cased by binding of ligands to ionophoric receptors. One embodiment of the structural portion of a surface detection array device suitable for use with a biosensor is shown in FIG. 4, as described above.

The device is connected to or interfaced with a processor, which stores and/or analyzes the signal from each array element. The processor in turn forwards the data to computer memory (either hard disk or RAM) from where it can be used by a software program to further analyze, print and/or display the results.

Biosensors employing arrays of independently-addressable receptor-containing lipid bilayer regions have a number of advantages over previously-available biosensors. For example, the bilayer membrane fluidity endows devices of the invention with surface properties similar to those of living cells (e.g., Chan, et al., 1991; Tözeren, et al., 1992). In one particularly compelling set of studies, it was shown that purified major histocompatibility complex protein incorporated into a supported membrane can effectively replace the antigen presenting cell in the presentation of a reprocessed antigen to a helper T-cell (McConnell, et al., 1986; Watts and McConnell, 1987).

1. Detection Methods. Receptor-based biosensors operate by detecting the specific binding of selected analytes to "receptor" biomolecules on the biosensor. Since the present invention employs fluid bilayers resembling cell membranes, virtually any transmembrane, membrane-anchored or membrane-associated protein can be used as the receptor. The receptor is incorporated into the lipid vesicles used to generate the bilayer expanses of the surface detector array devices. Binding of ligand to a receptor is typically detected either optically or electrically/electrochemically.

Optical detection methods include ellipsometry (Corsel, et al., 1986; Jönsson, et al., 1985; Vroman and Adams, 1969), optical wave guidance (Nellen and Lukosz, 1990) and surface plasmon resonance (SPR, Cullen, et al., 1988; Liedberg, et al., 1983). SPR is particular advantageous for monitoring molecular interactions in real-time, enabling a sensitive and comprehensive analysis of the degree of binding interactions between two proteins.

In this approach, support grid is produced by making a support grid of an array of conductive regions (e.g., gold) separated by bilayer barrier regions. A very thin polymer film (e.g., polyacrylamide or dextran; Elender, et al., 1996; Khuner, et al., 1994) is then deposited on the conductive regions to form bilayer-compatible surface regions. Khüner, et al., (1994) describe the coupling of polyacrylamide to a surface by 3-methacryl-oxypropyl-trimethoxy-silane (MPTS; Serva, Heidelberg, Germany).

Bilayers containing the selected molecules are deposited as described, and the bilayer-containing support grid is placed into a cell which allows a solution to be passed over the surface containing the array of receptor-studded lipid expanses. The grid is illuminated at an angle with a light-emitting diode (LED), and reflected light is analyzed with a photodetector. Through an evanescent electric field generated by the interaction of incident light with the gold layer, the reflected light is sensitive to the environment of a layer extending about 1 $\mu$m ($\lambda$=760 nm) from the receptors into the medium. Changes in the environment of the receptor, such as are caused by the binding of a ligand to the receptor, are detected as changes in the reflectance intensity at a specific angle of reflection (the resonance angle).

Capacitative detection or impedance analysis may also be used. Here, an electrode is incorporated into each the bilayer-compatible surface region, and a "ground" electrode is placed in the bulk aqueous phase. A voltage from a variable-frequency function generator is used to generate a selected voltage waveform which is fed across selected array elements. The peak-to-peak amplitude of the voltage is typically on the order of about 10 V, but can be substantially less. The voltage is applied over a range of frequencies and the capacitance is determined from the measured current as a function of signal frequency using standard signalprocessing techniques. Examples of the application of capacitance measurements and impedance analyses of supported bilayers are discussed, for example, in Stelzle, et al., (1993) and Stelzle and Sackmann (1989), both incorporated herein by reference.

Other methods of detection are discussed in U.S. Patents relating to biosensors, including Gitler, et al., 1993; Osman, et al., 1993; Taylor, et al., 1993; Case, et al., 1994; and Tomich, et al., 1994, all incorporated herein by reference.

2. Making of Biosensors. A surface detection array device is produced essentially as described above, except that (i) the vesicles used to make the bilayer expanse typically contain the desired receptor or biomolecule (although the receptor or biomolecule may also be introduced after the bilayer is formed), and (ii) different array elements are typically made with different vesicle suspensions.

Analyte selectivity is conferred to different array elements by different types of receptors present in the supported bilayer of each array element. Such distinct bilayer may be formed using liposomes or proteoliposomes containing the different biomolecules or receptors. A convenient method of making such a device is by depositing micro-droplets of the desired liposome suspension in the different compartments of a device substrate housed in a humidified chamber to eliminate fluid loss due to evaporation.

Any of several approaches known in the art can be used to form different-composition bilayers on a single microfabricated support grid. One suitable method employs a modified ink-jet printing device (Blanchard, et al., 1996, incorporated herein by reference) to deposit micro-drops containing selected vesicle suspensions on the individual bilayer-compatible surface regions of the device in a humidified chamber. The ink-jet print head of the device is modified to deliver small drops (e.g., ~100 $\mu$m in diameter) of vesicle-containing suspension in a high density array format. Adjacent drops may be deposited as close as 30 $\mu$m from one another. The barriers in such applications have a width that is typically on the order of the minimum separation distance between adjacent drops (i.e., ~30 $\mu$m), but can be greater or smaller in particular applications.

Of course, the vesicle suspensions may also be deposited using standard micropipeting technology (i.e., a micropipet in a holder connected to a micromanipulator). The micromanipulator may be controlled by a motorized drive for greater precision and efficiency. Such drives, as well as micromanipulators, are commercially available, e.g., from Newport Corp., (Irvine, Calif.) and Narashige USA, Inc. (Greenvale, N.Y.). The drive in turn can be controlled by a microcomputer for fully automated operation. The entire process can be monitored, if desired, using a conventional microscope, such as a dissecting microscope.

Suitable micropipettes may be made using a standard micropipet puller, such as a puller available from Narashige. The tips of the pipets can be made to have opening diameters ranging from less than a micron to tens of microns or more. The back of the pipet can be connected to a standard microinjection pump set to dispense a desired volume of vesicle suspension.

The drops containing the vesicle suspensions are allowed to incubate on the substrate grid for a few minutes to allow essentially all the membranes that are capable of forming to form. The grid is then gently flooded with aqueous solution until a suitable bulk aqueous phase is established above the bilayer membranes. A convenient method of flooding the grid without significantly disturbing the bilayers is to bring the level of aqueous in the chamber up until the surface is flush with the top of the grid, but the compartments still contain only the originallydeposited drops. The top of the grid is then exposed to a fine mist of the aqueous solution until the droplets coalesce into a uniform film of aqueous solution. The level of solution is then raised to a achieve a desired volume of bulk phase aqueous above the grid.

3. Use of Biosensors. A biosensor employing a biosensor surface detector array device such as described above can be used to detect low concentrations of biologically-active analytes or ligands in a solution containing a complex mixture of ligands. In such a method, the surface detector array device is constructed with different receptors in the bilayer expanses at different array positions. To control for signal fluctuations, several different array elements may contain the same type of receptor. Similarly, designated array elements may be used for positive and/or negative control purposes.

The biosensor surface detector array device is then contacted with an aqueous solution containing a mixture of ligands to be analyzed for the presence of selected ligands, such as receptor agonists, where the contacting takes place via the bulk aqueous solution portion of the device. In other words, the mixture to be tested is washed over the device, replacing the bulk aqueous portion. When a selected ligand specifically binds to a receptor, the binding is detected by a suitable detection method. For example, in an assay for the presence of acetylcholine (Ach) using an array device containing Ach receptors (AchRs) incorporated into the lipid expanse of at least one array element, the binding of Ach to the AchRs is detected as a change in the transmembrane voltage or current in the element containing the AchRs.

B. Substrate for Bioactivity Screens

In an embodiment related to the biosensor application described above, devices of the present invention may be used as substrates for holding an array of receptors employed in bioactivity screens of compounds. In particular, high-throughput screens of large libraries of compounds are typically optimized for speed and efficiency in order to rapidly identify candidate compounds for subsequent bioactivity testing. When such bioactivity testing involves, for example, assays for ion channel agonists or antagonist activity, the testing is often done one compound at a time by a scientist using electrophysiological measurements (e.g., patch clamping; see, e.g., Hamill, et al., 1981) of individual cells expressing the target ion channel or receptor. While this type of analysis provides detailed high quality data for each compound, it is slow and inefficient if a large number of compounds are to be assayed for bioactivity.

Devices of the invention may be used in secondary screen to assess the bioactivity of compounds identified in a high-throughput screen, enabling the scientists to focus on the few truly-interesting compounds. The devices are made essentially as described above for biosensors. The same types of binding-detection schemes may be employed, although when assaying compounds for bioactivity on ionotrophic receptors or ion channels, electrical detection is typically preferred to optical detection.

In devices employing electrical detection using electrodes in each of the array elements, it will be appreciated that since a water film separates the electrode from the bilayer, an electric field may be applied across the bilayer membrane, e.g., to activate voltage-dependent ion channels. This allows screening for compounds which only bind to the channel when the channel is in a state other than the resting state (e.g., in an activated or inactivated state).

In a related embodiment, devices of the invention are used as substrates for holding libraries (e.g., combinatorial libraries) of compounds. The bilayer expanses are deposited onto a support grid from a common bulk vesicle suspension, as detailed in Example 1, and each bilayer expanse region is then derivatized with a selected biomolecule, e.g., using one of the methods detailed above. One application if this approach is the use of light-directed synthesis (Fodor, et al., 1991) to generate spatially-addressable molecular libraries (e.g., peptide libraries) in a form where the peptides are displayed on the surface of the confined patches of fluid membrane. This is somewhat analogous to phage display, except that here the peptide sequence is defined by its location in the array. Such libraries may be particularly useful for cell screening due to the native-like surface provided by the membrane.

C. Forming Regions with a High Density of Membrane Proteins

The invention also includes a method of forming supported bilayers with regions of very high membrane protein density. As stated above, protein-containing vesicles, or proteoliposomes, can typically only be formed with a protein:lipid mole ratio of about 1:500 or lower—vesicles with higher mole ratios do not consistently form uniform planar bilayers. Accordingly, high-density arrays of proteins in lipid bilayers cannot be formed by simply fusing protein-containing vesicles with a surface to form a supported bilayer.

Figure 3:
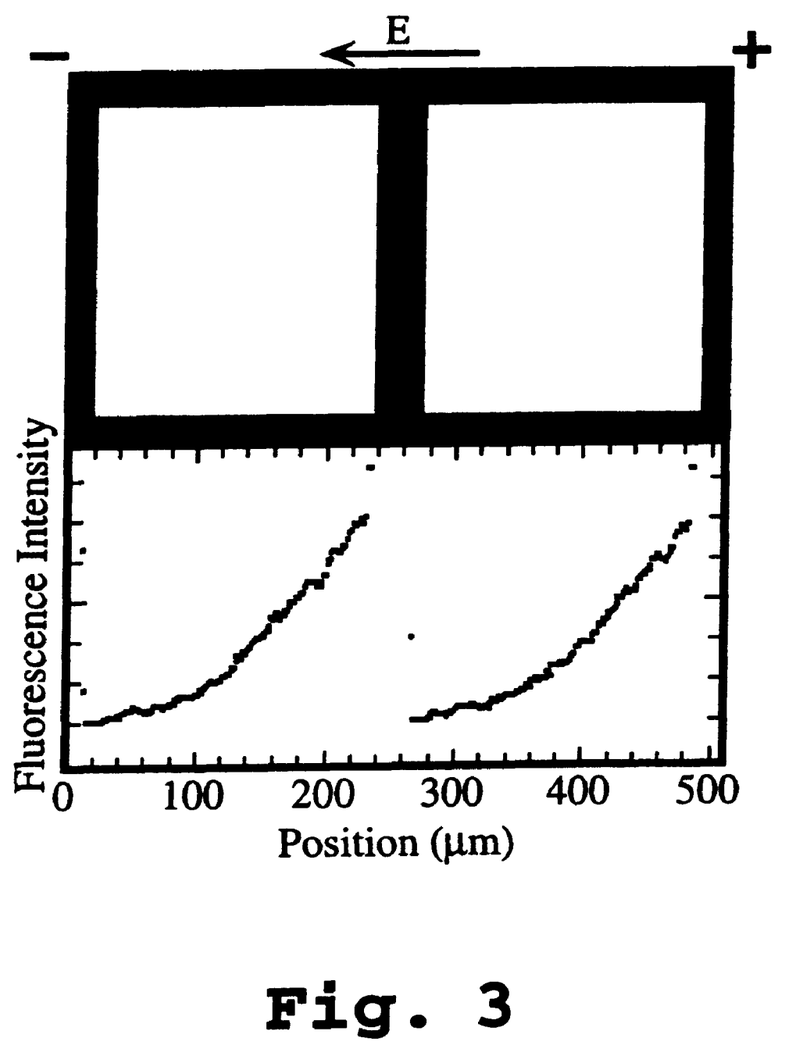
FIG. 3 shows the fluorescence intensity from two regions of a surface detector array device, each containing a field-induced concentration gradient of charged fluorescent reporter lipids.

As shown in Example 3 and FIG. 3, however, if the supported bilayer is formed in a corral surrounded by bilayer barrier regions and subjected to an electric field, the membrane proteins can be concentrated into regions of very high density. This effect can be amplified by, for example, making the migration focal point the apex of a triangular corral.

After the proteins have been concentrated, they can be used for subsequent applications, such as diffraction studies to determine structure. If desired, the high-density protein region of the field-induced concentration gradient can be "frozen" by cross-linking the proteins using standard cross-linking methods (e.g., treatment with glutaraldehyde).

D. Device for Measuring Receptor Size and/or Aggregation

Another aspect of the invention relates to sorting devices for biomolecules integrated into or attached to the supported bilayer. The sorting devices employ the bilayer barrier surface regions not to compartmentalize the surface into discrete patches, but rather, to act as 2-dimensional sieves having progressively smaller "openings" from one end of the device to the other. One embodiment of the structural portion of this aspect of the invention is shown in a top view in FIG. 5. Here, the structural portion of the device 70 is formed of a wafer 72 having a substrate surface 74 defining a bilayer-compatible region bounded on all sides by a bilayer barrier region 76. The bilayer-compatible region is also interrupted by a plurality of substantially parallel broken lines 78 defining bilayer barrier surface regions. The gaps in the lines are of molecular dimensions and get progressively smaller going from one edge 80 of the device to the opposite edge 82. Electrodes 84, 86 are positioned near the edges of the device and are connected to a voltage source 88 via wires 90.

Figure 5:
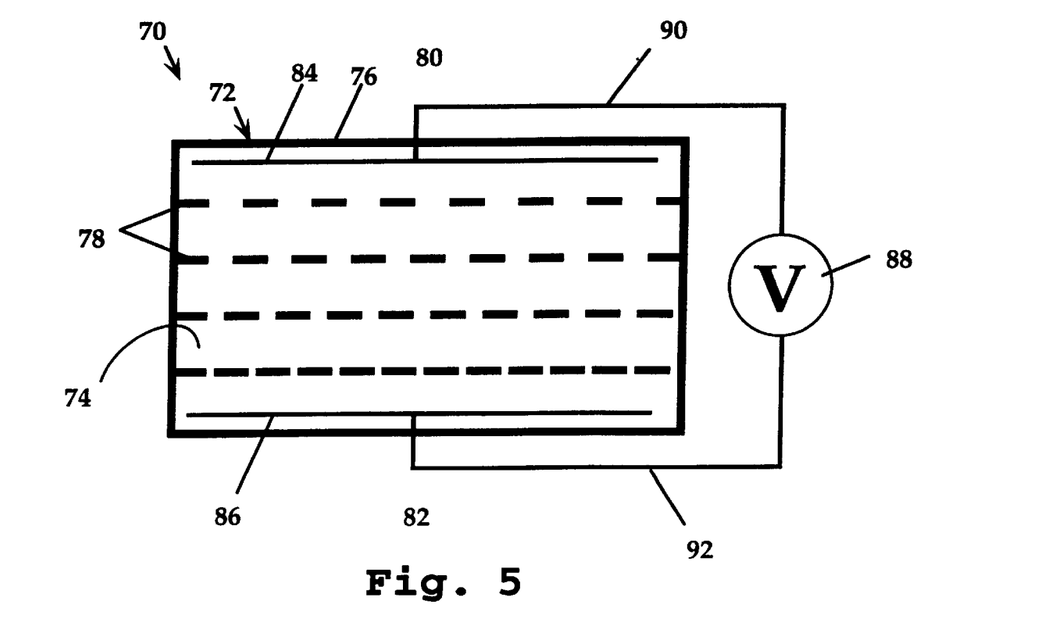
FIG. 5 shows the structural portion of a device of the invention suitable for use in separating membrane-associated molecules by size.

The device is employed to sort membrane-associated molecules by size. A mixture of like-charged molecules having different sizes is loaded in the well formed by the bilayer barrier region circumscribing and the broken line having the largest gaps. The voltage source is turned on with a polarity to cause the charged biomolecules to migrate through the progressively smaller gaps of the consecutive barriers until they get trapped according to size in the well defined on the "downstream" side by a barrier having gaps too small for the molecules to pass through.

In a related application, the bilayer barrier regions are arranged to provide a uniform or graded array or network of barriers, and electrophoresed membrane molecules are sorted based on the migration time through the array. Here, the method of separation is similar to that obtained with a gel, such as an agarose or polyacrylamide gel, where smaller molecules migrate faster than larger molecules.

The following examples illustrate but in no way are intended to limit the present invention.

MATERIALS AMD METHODS

Unless otherwise indicated, chemicals were purchased from Sigma (St. Louis, Mo.) or United States Biochemical (Cleveland, Ohio).

A. Buffers

Standard Buffer 10 mM Tris 100 mM NaCl (pH 8.0)

Phosphate-buffered saline (PBS)

10×stock solution, 1 liter:

80 g NaCl 2 g KCl 11.5 g $Na_2HPO4$-$7H_2O$ 2 g $KH_2PO_4$

Working solution of PBS, pH 7.3:

137 mM NaCl 2.7 mM KCl 4.3 mM $Na_2HPO_4$-$7H_2O$ 1.4 mM $KH_2PO_4$

B. Lipids and Labels

L-α phosphatidylcholine from egg (egg-PC) were obtained from Avanti Polar Lipids (Alabaster, Ala.). The fluorescent probe N-(Texas Red sulfonyl)-1,2-dihexadecanoyl-sn-glycero-3-phosphoethanolamine, triethylammonium salt (Texas Red DHPE) was obtained from Molecular Probes (Eugene, Oreg.).

C. Preparation of Phospholipid Vesicles

Small unilamellar vesicles (SUVs) were prepared by following the protocol outlined in Barenholz, et al. (1977) using egg L-α phosphatidylcholine (Avanti). The phosphatidylcholine was mixed with 1 mole % Texas red DHPE in HPLC-grade chloroform (Sigma-Aldrich) and dried in a vacuum desiccator overnight. The dried lipids were resuspended to about 6 mg/ml in standard buffer which had been filtered through Rainin Nylon-66 0.45 μm filters using a Sibata filter unit. The suspension was sonicated to clarity with a Branson ultrasonicator under flowing Ar on ice for 3 minute periods separated by 1 minute cooling periods (Martin, 1990). The sample was then spun for 30 minutes at 100,000 Xg to remove Ti particles from the sonicator tip, and the supernatant was spun for 4 hours at 166,000 Xg to obtain the SUVs. The SUVs were stored at 4° C. under $N_2$ or Ar in the dark and were used within three weeks. The lipid concentration in these samples was determined from the Texas Red probe absorption at 590 nm ($\epsilon$=100,000 $M^{-1}$ $cm^{-1}$; Haugland, 1992) assuming that the probe concentration in the vesicles is 1 mole % as prepared. Yields (mg SUV lipid/mg initial lipid) are calculated from this concentration and are equal to those reported by Barenholz, et al. (1977).

D. Membrane Electrophoresis

For the electrophoretic studies, the supported membrane in PBS was diluted to 1 mM total ionic strength. This was then assembled, under buffer, into a sandwich with another coverslip. The electrophoresis cell consisted of two 0.01" diameter platinum wire electrodes in solution-filled wells of a Teflon trough. The coverslip sandwich was arranged to form a bridge between the two electrode wells. Electrical connection was achieved through the solution in the cover slip sandwich. Fields up to 60 V/cm were applied with a standard power supply. Currents were monitored with a Keithley picoammeter (Cleveland, Ohio) and were typically around 3 μA for a single 18 mm square coverslip sandwich at 15 V/cm. This corresponds to a total power dissipation of $9 \times 10^{-5}$ W which should produce a negligible amount of Joule heating.

EXAMPLE 1

Construction of a Surface Detector Device

A patterned support grid was microfabricated using standard techniques (Wolf and Tauber, 1986). 100 mm diameter silicon 1-0-0 wafers were obtained from Silrec Corporation (San Jose, Calif.). The wafers were maintained in steam at 1000° C. in an oxidation furnace (Tylan Inc., San Diego, Calif.) to generate a ~1 μm thick layer of thermal oxide. Standard positive photoresist (S-1800; Shipley Inc., Marlborough, Mass.) was spun onto the wafers at a thickness of one micron with a track coater (Silicon Valley Group, San Jose, Calif.).

The wafers were exposed for ~8 seconds to ~10 mW/cm$^2$ UV light through a photolithographic mask with a contact mask aligner (Karl Suss America (Waterbury Center, Vt.), MA-4). Development was done on a track developer (SVG) using standard tetramethylammonium hydroxide (TMAH)-based developer (Shipley). The wafers were then subjected to a three minute etch in argon plasma.

Membranes were formed by contacting the patterned surface of the wafer support grids with a suspension, prepared as described above, containing ~25 nm diameter unilamellar vesicles consisting primarily of L-α-phosphatidylcholine (PC) molecules doped with 1 mole percent of the fluorescently labeled lipid, Texas Red DHPE. Vesicles in the suspension spontaneously assembled in a matter of seconds to form a continuous single bilayer on the bilayer-compatible regions of the support grid, as evidenced by photobleaching and electrophoresis experiments described below.

Excess vesicles were rinsed away while maintaining the membrane under the bulk aqueous solution at all times. Results of extended experiments monitoring the state of the supported bilayers indicated that the bilayers are stable under water and retain their uniformity and fluidity for a period of weeks.

EXAMPLE 2

Fluidity of Supported Bilayers Assayed by Photobleaching

Figure 2A:
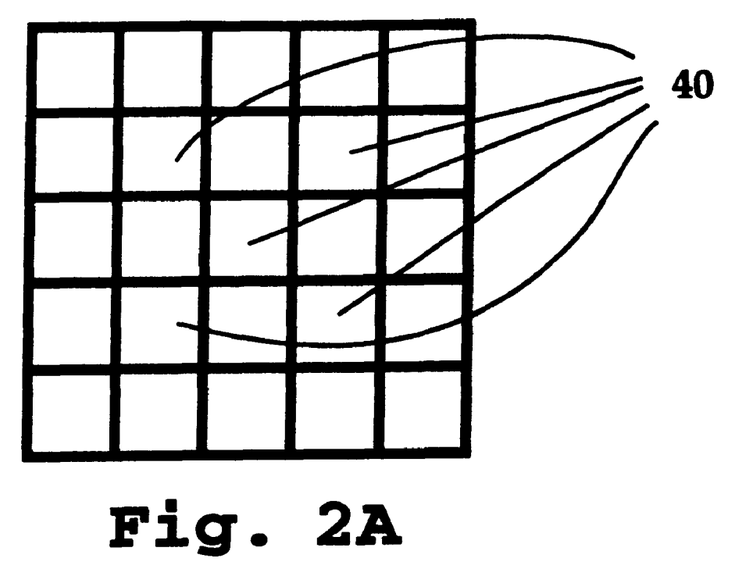
FIGS. 2A and 2B are schematics illustrating the effect of photobleaching fluorescent reporter lipids in the lipid bilayers of five distinct regions of a surface detector array device of the invention.

Long-range fluidity within the bilayer-compatible regions, or corrals, was observed by fluorescence recovery after photobleaching (FRAP). The experiment is described with respect to FIGS. 2A and 2B, which show schematics of a surface detector array device containing 25 bilayer-compatible surface regions, or corrals, with a corresponding lipid bilayer expanse carried on each of these surface regions. The device was made from an oxidized silicon wafer patterned with photoresist to generate corrals dimensioned 100 μm per side. The 10 μm wide photoresist (bilayer barrier regions) appears as the black boundaries separating the 25 corrals in FIGS. 2A and 2B. Texas Red DHPE lipid probe (Molecular Probes, Eugene, Oreg.) was incorporated in the bilayer membrane to serve as a label.

Figure 2B:
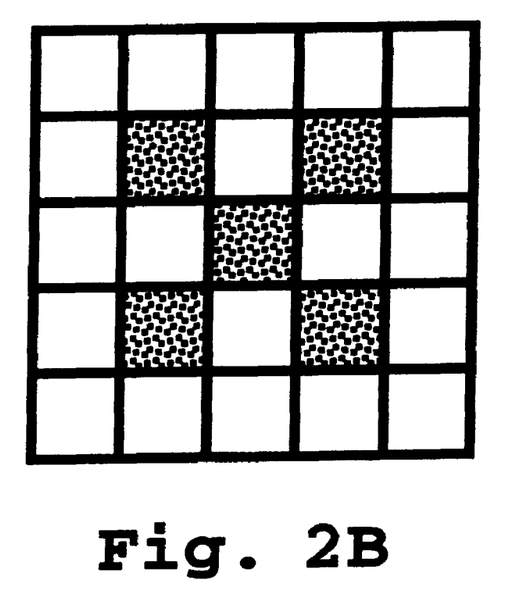

A circular beam of light having a diameter of less than 100 μm was used to photobleach the fluorescent probe molecules in five individual corrals 40 (FIG. 2A), yielding the results schematized in FIG. 2B. Diffusive mixing of molecules within each corral caused the circular bleached spot to spread, filling the square corral. The lines of photoresist acted as barriers to lateral diffusion, preventing mixing between separate corrals. Fluidity of the membrane was evidenced by the spreading of the bleached region to fill each square corral. If the membrane had not been fluid, a circular bleached (dark) region would have remained.

Bleach patterns such as those illustrated in FIG. 2B were stable for many days, whereas spots photobleached into a single continuous membrane with no such barriers diffused away completely in about 30 minutes.

EXAMPLE 3

Fluidity of Supported Bilayers Assayed by Electrophoresis

The fluidity of the supported bilayers on the bilayer-compatible surface regions was also assessed by electrophoretic redistribution of charged membrane components. This method illustrates both the fluidity of the lipid bilayer and confinement of different-composition bilayer patches to distinct independently-addressable bilayer-compatible surface regions.

A device with 200 μm square corrals was prepared as described above using PC molecules doped with 1 mole percent of the fluorescently labeled lipid, Texas Red DHPE (Molecular Probes).

An electric field of 15 V/cm was applied parallel to the lipid bilayer membrane. Upon application of the field, the charged molecules (labelled DHPE) drifted in the plane of the bilayer, whereas the neutral PC molecules, forming the bulk of the membrane, were unaffected by the field. Application of the field for ~25 minutes resulted in a steady-state, electric field-induced concentration profile (Groves and Boxer, 1995) of the negatively-charged fluorescent probe.

A quantitative description of the field-induced concentration gradient is depicted in FIG. 3, which shows quantitative traces of fluorescence intensity calculated from videomicrographs of steady-state concentration gradients of the fluorescent probe lipid (Texas Red DHPE) in two 200 μm microfabricated corrals. The concentration gradients in this experiment adopted an exponential profile. The image from which the fluorescence intensity traces were calculated was taken with a low light level video camera which had been adjusted for linear imaging of fluorescence intensity.

The field-induced concentration gradients were fully reversible, taking approximately the same amount of time to dissipate as they took to form at 15 V/cm. The profiles could be switched by reversing the polarity of the field repeatedly without any apparent effect on the membrane or the bilayer-barrier regions, or barriers. The field-induced concentration profiles described above can be used to study molecular size, clustering, and non-ideal mixing.

EXAMPLE 4

Bilayer Barrier Regions Do Not Function by Mechanically Separating Adjacent Bilayer Expanses Experiments were performed to determine whether the bilayer barrier regions isolate adjacent bilayer expanses by mechanical separation or by intrinsic properties of the material making up the bilayer barrier surface regions. Bilayer membranes were deposited on unpatterned $SiO_2$ substrates (i.e., a substrate having a single bilayer-compatible surface) as described above. However, the topography of the bilayer-compatible surface was the same as that of the photoresist-patterned $SiO_2$ substrate described above.

Continuity of the bilayer(s) was assayed using the FRAP and electrophoretic methods described above. The results indicated that the lipid expanse was a single supported membrane which followed the contours of the corrugated surface without disruption.

EXAMPLE 5

Generation of an Array Device with Electrodes Under the Supported Bilayers

This example describes the making of silicon electrodes covered by a thin layer of silicon dioxide. Bond pads may be used to connect wires to the silicon electrodes.

A. Wafers

Silicon-on-oxide wafers were purchased from Ibis Technology Corporation, Danvers, Mass. The wafers are 100 mm in diameter and approximately 500 $\mu$m thick. As supplied by the manufacturer, the wafers have a ~0.4 $\mu$m thick silicon dioxide layer buried under a ~0.2 $\mu$m thick layer of pure silicon, which forms the top surface of the wafer.

B. Pre-resist Clean and Resist Coating

The wafers were cleaned with a conventional RCA cleaning procedure (Kern and Puotinen, 1970; Wolf and Tauber, 1986, p. 516), baked at 150° C. for 30 minutes, and coated with 1 $\mu$m of photoresist (Shipley S-1813) using conventional spin coating with a Silicon Valley Group (SVG) track coater system.

C. Exposure and Development

The mask pattern was exposed using an 8 second exposure on a Karl Suss MA-4 contact mask aligner with an electron beam master mask consisting of chrome patterns on a quartz substrate. The wafers were then soaked in chlorobenzene for 15 minutes before developing with standard TMAH (tetramethylammonium hydroxide) based developer (Shipley) using a Silicon Valley Group track developer system.

D. Etch and Thin Oxide Growth

The electrode patterns were etched into the top silicon layer using a conventional fluorine based plasma etch (Wolf and Tauber, 1986), which selectively etches silicon, but not silicon dioxide. The gases used in the plasma etch were $SF_6$, $O_2$, and $CHF_3$. Following a second RCA clean, a thin oxide was grown at 1000° C. in a steam oven to a thickness of 0.1 $\mu$m.

E. Pattern for Bond Pads

Another RCA clean is performed and a new layer of resist is deposited as described above. A new pattern, which defined openings in the oxide layer grown in the previous step, was transferred to the resist by photolithography as described above and the exposed resist was developed as described above.

F. Etch Openings for the Bond Pads

The wafers were etched in an Applied Materials (Santa Clara, Calif.) reactive ion etcher to open holes in the top oxide layer so that contacts to the underlying silicon layer could be made for bond pads.

G. Evaporate Gold

A 0.3 $\mu$m layer of gold was evaporated on the wafer before the resist from the previous step was removed. This gold was then lifted off with acetone, resulting in gold bond pads located in the holes which were etched in the previous step.

While the invention has been described with reference to specific methods and embodiments, it will be appreciated that various modifications may be made without departing from the invention.

It is claimed:

1. A surface detector array device, comprising a substrate having a surface defining a plurality of distinct bilayer-compatible surface regions separated by one or more bilayer barrier regions, wherein said bilayer-compatible surface regions and said bilayer barrier surface regions are formed of different materials, a lipid bilayer expanse stably localized on each of said bilayer-compatible surface regions, and an aqueous film interposed between each bilayer-compatible surface region and corresponding lipid bilayer expanse, wherein each lipid bilayer expanse is stably localized above each bilayer-compatible surface in the absence of covalent compatible surface, and separated therefrom by said aqueous film, and a bulk aqueous phase covering the lipid bilayer expanses.

2. The detector of claim 1, wherein the bilayer-compatible surface region is formed from a material selected from the group consisting of $SiO_2$, $MgF_2$, $CaF_2$, and mica.

3. The detector device of claim 2, wherein the bilayer-compatible surface region is formed from $SiO_2$.

4. The detector device of claim 1, wherein the bilayer barrier surface region is formed from gold.

5. The detector device of claim 1, wherein the bilayer barrier surface region is formed from positive photoresist.

6. The detector device of claim 1, wherein the bilayer barrier sueface region is formed from aluminum oxide.

7. The detector device of claim 1, wherein the lipid bilayer expanse comprises at least one lipid selected from the group consisting of phosphatidylcholine, phosphatidylethanolamine, phosphatidylserine, phosphatidic acid, phosphatidylinositol, phosphatidylglycerol, and sphingomyelin.

8. The detector device of claim 7, wherein the lipid bilayer expanse comprises phosphatidylcholine.

9. The detector device of claim 1, wherein the device contains between about 10 and about 100 distinct bilayer-compatible surface regions.

10. The detector device of claim 1, wherein the device contains at least about 2500 distinct bilayer-compatible surface regions.

11. The detector device of claim 1, wherein the device contains at least about 25,000 distinct bilayer-compatible surface regions.

12. The detector device of claim 1, wherein the device contains at least about 2.5 million distinct bilayer-compatible surface regions.

13. The detector device of claim 1, wherein the bilayer-compatible surface regions are separated from one another by bilayer barrier regions that are between about 1 $\mu$m and about 10 $\mu$m in width.

14. The detector device of claim 1, wherein lipid bilayer expanses on different bilayer-compatible surface regions have different compositions.

15. The detector device of claim 1, wherein lipid bilayer expanses further include a selected biomolecule and different expanses have different biomolecules.

16. The detector device of claim 15, wherein the biomolecule is a transmembrane receptor or ion channel.

17. The detector device of claim 15, wherein the biomolecule is covalently attached to a lipid molecule.

18. A surface detection array device for use in a biosensor, comprising a substrate having a surface defining a plurality of distinct bilayer-compatible surface region separated by one or more bilayer barrier regions, said bilayer-compaLible surface regions and said bilayer barrier regions being formed of different materials, a lipid bilayer expanse stably localized on each of the bilayer-compatible surface regions, an aqueous film interposed between each bilayer-compatible surface region and corresponding lipid bilayer expanse, wherein each lipid bilayer expanse is stably localized above each bilayer-compatible surface in the absence of covalent linkages between each lipid bilayer expanse and each bilayer-compatible surface, and separated therefrom by said aqueous film, and wherein each bilayer expanse contains a specie of receptor or biomolecule, and different bilayer expanses contain different species of receptors or biomolecules, and a bulk aqueous phase covering said lipid bilayer expanses.

* * * * *

UNITED STATES PATENT AND TRADEMARK OFFICE
CERTIFICATE OF CORRECTION

PATENT NO. : 6,228,326 B1　　　　　　　　　　　　　　　　　　　　　Page 1 of 1
DATED : May 8, 2001
INVENTOR(S) : Steven G. Boxer, Morrison Ulman, and John T. Groves It is certified that error appears in the above-identified patent and that said Letters Patent is hereby corrected as shown below:

<u>Title page,</u>
Inventors section, "Nick Ulman" should be -- Morrison Ulman -- and "Jay T. Groves" should be -- John T. Groves --.

Signed and Sealed this

Thirtieth Day of October, 2001

Attest:

*Nicholas P. Godici*

NICHOLAS P. GODICI
*Attesting Officer*　　*Acting Director of the United States Patent and Trademark Office*